United States Patent [19]

Tiffany

[11] Patent Number: 4,872,877

[45] Date of Patent: Oct. 10, 1989

[54] INTRAOCULAR LENS WITH ULTRAVIOLET SCREENING AGENT

[75] Inventor: John Tiffany, Ventura, Calif.

[73] Assignee: Dennis T. Grendahl, Shorewood, Minn.

[21] Appl. No.: 26,631

[22] Filed: Mar. 17, 1987

[51] Int. Cl.$^4$ ................................. A61F 2/16
[52] U.S. Cl. .......................... 623/6; 623/901; 8/507; 8/638; 351/160 R; 351/160 H
[58] Field of Search ............... 8/467, 507, 648, 638; 250/519.1; 351/160 R, 160 H, 163, 166; 523/106, 107; 623/4, 5, 6, 901

[56] References Cited

U.S. PATENT DOCUMENTS

| | | | |
|---|---|---|---|
| 4,021,471 | 5/1977 | Virgilio et al. | 524/237 |
| 4,189,546 | 2/1980 | Deichert et al. | 623/1 |
| 4,217,038 | 8/1980 | Letter et al. | 351/160 R |
| 4,238,524 | 12/1980 | LaLiberte et al. | 8/507 |
| 4,257,692 | 3/1981 | La Naour-Sene | 351/159 |
| 4,304,895 | 12/1981 | Loshaek | 523/106 |
| 4,478,876 | 10/1984 | Chung | 522/14 |
| 4,636,212 | 1/1987 | Posin et al. | 623/6 |

FOREIGN PATENT DOCUMENTS 0136882 8/1983 Japan ........................ 8/507

*Primary Examiner*—Richard J. Apley
*Assistant Examiner*—Paul Prebilic
*Attorney, Agent, or Firm*—Hugh D. Jaeger

[57] ABSTRACT

An ultraviolet screening agent can be incorporated into a preformed silicone rubber intraocular lens by bringing it into contact with a solution which contains the agent in a higher concentration than the lens material.

6 Claims, No Drawings

INTRAOCULAR LENS WITH ULTRAVIOLET SCREENING AGENT

BACKGROUND OF THE INVENTION

1. Field of the Invention

This invention relates to the field of foldable or elastomeric implantable intraocular lenses composed primarily of transparent silicone, and more particularly, pertains to a method for incorporating ultraviolet screening agents into such lenses.

2. Description of the Prior Art

Poly (methyl methacrylate), such as Perspex CQ from Imperial Chemical Industries (ICI), has been used for a number of years for intraocular lenses. Early implantable intraocular lenses were designed to replace cataract-damaged natural lenses, and were generally made of poly (methyl methacrylate). Ultraviolet screening agents were later added to the polymeric lens formulations because of concern over possible ultraviolet radiation damage to the retina.

Typical compounds used to impart ultraviolet protection to poly (methyl methacrylate) fall primarily into one of two classes, hydroxybenzophenones and their derivatives, or hydroxybenzotriazoles and their derivatives. These materials are available commercially under a number of different trade names and absorb different wavelengths of ultraviolet radiation depending on their substitute groups. Most of these compounds are effective in blocking transmission of 90% of the ultraviolet radiation below a wavelength of 400 nm when used at concentrations below 1% by weight in a plastic sheet 1 mm thick.

Transparent silicone lenses were developed later because the lenses allowed for insertion through a smaller incision by folding the lens.

Many of the same ultraviolet screening agents may be mixed into the silicone rubber compounds before they are fabricated into lenses and cured. However, in the interests of increased production volume, the silicone lenses are formed in mold cavities with the application of heat. These conditions produce an undesirable yellow color when ultraviolet screening agents are present. The screening agents also retard or inhibit the cure of some types of silicone resulting in undesirable weak and soft lenses. Additionally, when silicone lenses are treated to prevent fogging when immersed in water, some of the screening agents may be lost by leaching from the silicone matrix.

The shortcomings are minimized in the lenses of the present invention which are made by using diffusion to incorporate the ultraviolet screening agent into the lens after it has been shaped and cured.

SUMMARY OF THE INVENTION

The lenses themselves are preformed of any silicone material customarily used in their fabrication. Illustrative are McGhan NuSIL MED-6210 A/B, Petrarch Systems PSW 2398 A/B. These materials are all either resin-reinforced dimethyl siloxanes or resin reinforced copolymers of dimethyl and diphenyl siloxanes containing 4–12 percent diphenyl siloxane.

Preferred for use are McGhan NuSIL MED-6210 A/A or Shin-Etsu KE 1935 A/B.

The lenses are made by conventional techniques, ordinarily molding or casting.

The ultraviolet screening agents can be o-hydrophenyl ketones such as O-hydroxybenzophenones; hydroxybenzotriazoles such as 2-(2-hydroxyphenyl) benzotriazoles; and substituted or unsubstituted phenylformamidines. Preferred for use according to the invention are 2,2'-dihydroxy-4,4'-dimethoxybenzophenone (Uvinul D-49) and 2-(2'-hydroxy-5'-methyl phenyl)benzotriazole (Tinuvin P).

The screening agents can be used alone or in combination.

(The optimum benzotriazole identified to date is 2(3',5'-di-tert-butyl-2'-hydroxyphenyl)-5-chlorobenzotriazole.)

DESCRIPTION OF THE PREFERRED EMBODIMENTS

Lenses are made according to the invention by first preparing a solution of a screening agent in an organic liquid. Any liquid may be used provided the liquid will dissolve the required amount of agent, will not significantly degrade the lens material, and is physiologically acceptable. Illustrative are lower alcohols (methanol, ethanol, isopropanol), lower ketones (propanone, butanone), ethyl acetate, tetrahydrofuran, aromatics (benzene, toluene, xylene).

Isopropanol is preferred.

The concentration of screening agent in the the liquid is dictated by the nature of the silicone used to fabricate the lens, and must be such that the solution has a higher concentration of absorber than the lens material. Ordinarily, a concentration of 0.05–0.5%. by weight, will give a solution having the requisite concentration.

A preformed lens is then immersed in the solution, or otherwise brought into contact with it, and is then held at a temperature of 20°–40° C. until the solution and lens reach osmotic equilibrium, determined by the ultraviolet absorption at 400 nm reaching a constant value. This ordinarily takes 2–10 days. The lens is then separated from the solution, rinsed and dried to constant weight, and is then ready for use.

Those skilled in this art will be able to practice the invention more easily after referring to the following illustrative example.

These artisans will no doubt be able to compose numerous variations on the theme disclosed, such as changing the amounts of components slightly but insignificantly from those shown, adding innocuous substances, or substituting equivalent or nearly equivalent components for those shown. All such variations are considered to be within the inventive concept.

MODE OF OPERATION

A solution is prepared by dissolving 0.0316 g of Uvinul D-49 in the 12.77 ml of isopropanol.

A piece of cured silicone rubber 2 mm thick and weighing 1.3 g is then immersed in the solution for three days at 25° C. It is then removed and dried at 80° C. to constant weight. Its UV absorbance is found to be one absorbance unit at 382 nm. The rubber is colorless and shows no change in hardness.

Various modifications can be made to the present invention without departing from the apparent scope thereof.

We claim:

1. A method for incorporating an ultraviolet screening agent into a preformed flexible silicone rubber intraocular lens, the method comprising:
   a. preparing a solution of an ultraviolet screening agent in an organic liquid, the concentration of agent in the solution being such that the solution has a higher concentration of agent than the lens material;

b. bringing the lens and the solution into contact with each other until the lens and solution reach osmotic equilibrium;

c. separating the lens and the solution; and, d. drying the lens.

2. The method of claim 1 wherein the screening agent used is an o-hydroxyphenyl ketone, a hydroxybenzotriazole, or a phenylformamidine.

3. The method of claim 2 wherein the screening agent is 2,2'-dihydroxy-4,4'-dimethoxybenzophenone.

4. The method of claim 2 wherein the screening agent is 2-(2-hydroxy-4-methylphenyl)-benzo triazole.

5. The method of claim 2 wherein the screening agent is a phenylformamidine.

6. The method of claim 1 wherein the screening agent used is 2(3',5'-di-tert-butyl-2'-hydroxyphenyl)-5-chlorobenzotriazole.

* * * * *